United States Patent
Schwarz-Hartmann et al.

(10) Patent No.: US 8,196,245 B2
(45) Date of Patent: Jun. 12, 2012

(54) ELECTRIC TOOTHBRUSH

(75) Inventors: Armin Schwarz-Hartmann, Wendelsheim (DE); Martin Haas, Eschborn (DE); Manfred Ringelmann, Eschborn (DE); Philipp Jung, Griesheim (DE); Michael Schmid, Frankfurt am Main (DE); Heiko Bornheimer, Wiesbaden (DE); Thomas Fritsch, Eppstein (DE)

(73) Assignee: Braun GmbH, Kronberg (DE)

( * ) Notice: Subject to any disclaimer, the term of this patent is extended or adjusted under 35 U.S.C. 154(b) by 859 days.

(21) Appl. No.: 12/162,410

(22) PCT Filed: Dec. 13, 2006

(86) PCT No.: PCT/EP2006/011969
§ 371 (c)(1),
(2), (4) Date: Dec. 4, 2008

(87) PCT Pub. No.: WO2007/085289
PCT Pub. Date: Aug. 2, 2007

(65) Prior Publication Data
US 2009/0188058 A1   Jul. 30, 2009

(30) Foreign Application Priority Data
Jan. 27, 2006 (DE) .......................... 10 2006 004 146

(51) Int. Cl.
*A46B 13/02* (2006.01)
*A61C 17/40* (2006.01)
(52) U.S. Cl. .................................... 15/22.1; 15/22.2
(58) Field of Classification Search ................... 15/22.1, 15/22.2
See application file for complete search history.

(56) References Cited

U.S. PATENT DOCUMENTS

| 3,196,299 A | 7/1965 | Kott |
| 3,967,617 A | 7/1976 | Krolik |
| 4,149,291 A | 4/1979 | Stoltz |
| 2005/0120496 A1* | 6/2005 | Miller et al. .................... 15/22.1 |
| 2005/0177962 A1* | 8/2005 | Chan .............................. 15/22.1 |

FOREIGN PATENT DOCUMENTS

| DE | 295 15 288 | 1/1996 |
| DE | 697 21 313 | 3/2004 |
| WO | WO03/005924 | 1/2003 |

* cited by examiner

*Primary Examiner* — Randall Chin
(74) *Attorney, Agent, or Firm* — Vladimir Vitenberg

(57) ABSTRACT

An electric toothbrush is provided, the electric toothbrush having a housing, with a drive that is elastically mounted on the housing by means of a spring device and can be moved in an oscillatory fashion in at least one plane of motion, and with a transmission element that is connected to the drive and serves for transmitting the driving motion to a brush head.

26 Claims, 3 Drawing Sheets

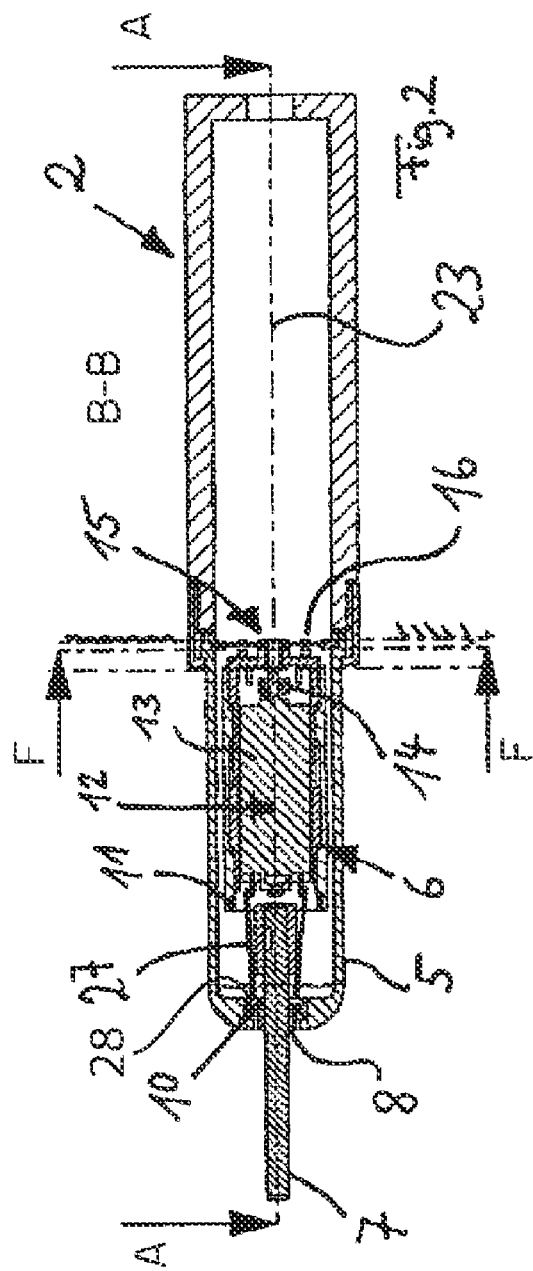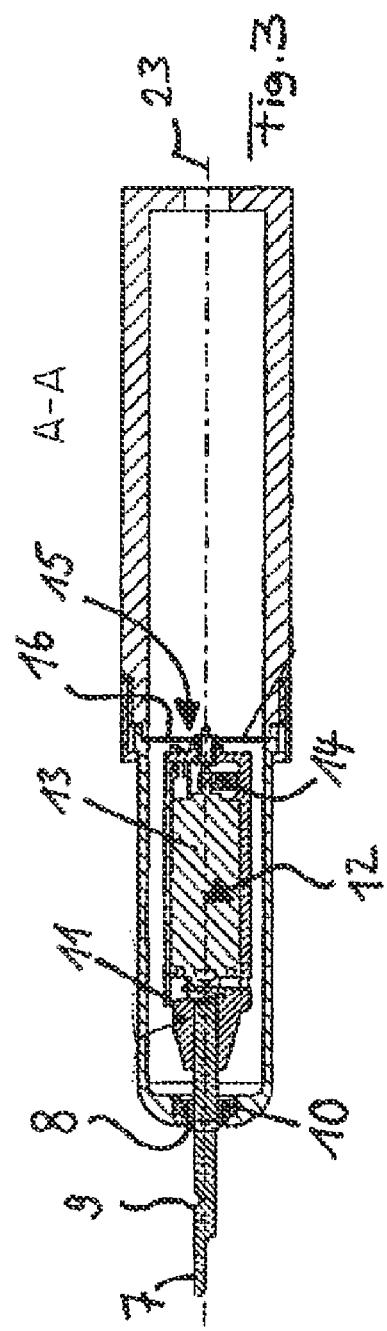

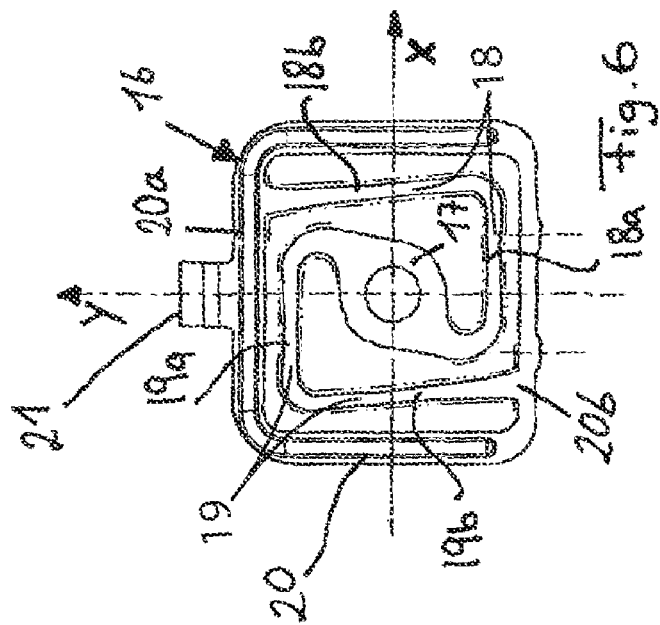
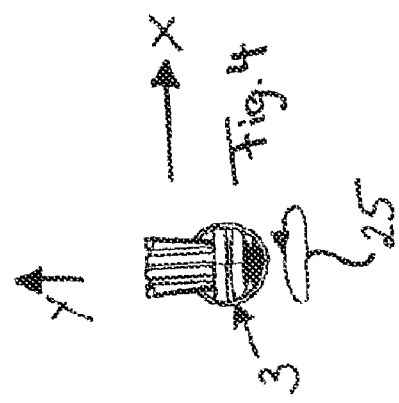

ELECTRIC TOOTHBRUSH

This application is the national stage of International Application No. PCT/EP2006/011969 filed Dec. 13, 2006, which claims priority under 35 U.S.C. §119(a) to German Application No. 10 2006 004 146.1, filed Jan. 27, 2006, the entire contents of which are hereby incorporated by reference.

TECHNICAL FIELD

The present invention pertains to an electric toothbrush, that includes a housing, a transmission element and a drive that is elastically mounted on the housing by means of a spring device and can be moved in an oscillatory fashion in at least one plane of motion. The transmission element is connected to the drive and serves for transmitting the motion of the drive to a brush head that can be attached to the transmission element.

BACKGROUND

An electric toothbrush in which the entire driving motor vibrates and these vibrations are transmitted to the brush head, is known from U.S. Pat. No. 3,196,299. The driving motor drives an imbalance in the form of an eccentrically supported mass and forms a vibratory drive together with this imbalance. The driving motor is arranged in a chassis that, in turn, is movably arranged on the housing of the toothbrush by means of a spring. The vibrations of the drive are transmitted to a transmission rod that is movably arranged in the housing and to which a clip-on brush can be attached. The spring is clamped between corresponding shoulders of the chassis and the housing and arranged at a through-opening of the housing between the clip-on brush and the driving motor. In this case, a relatively complicated screw mechanism is provided for changing the spring prestress in order to thusly vary and adapt the intensity of the vibrations or the motion amplitude of the drive to the requirements of different users. Despite this adjustability, one unsatisfactory aspect of such vibratory drives can be seen in that the brush head carries out an excessively intense poking motion while the wiping motion parallel to the tooth flanks is comparatively weak. In addition to a limited efficiency, this can lead to the user experiencing an unpleasant sensation while the toothbrush is used.

SUMMARY

In one aspect, the invention features a hand part of an electric toothbrush, including a housing, a drive that is elastically mounted on the housing by means of a spring device and can be oscillated in at least one plane of motion, and a transmission element that is connected to the drive and serves for transmitting the driving motion to a brush head. The spring device has different spring constants in two different directions in the aforementioned plane of motion of the drive such that the oscillatory motion of the brush head has different amplitudes in the these directions.

As a result, the direction of the generated driving motion of the elastically suspended drive, and therefore the cleaning motion of the brush head of the toothbrush is controlled, particularly such that said driving motion has different amplitudes in different directions. According to the invention, the spring device that serves for elastically mounting the drive on the housing has different spring constants in two directions in the plane of motion of the drive that preferably extend perpendicular to one another, namely such that the driving motion of the drive has different amplitudes in these directions. This makes it possible to adjust the intensity of the vibrations in different cleaning directions.

In some implementations, this makes it possible, in particular, to reduce the intensity of the poking motions of the brush head, i.e., motions that are essentially directed parallel to the bristles of the brush head, while the intensity of the wiping motions, i.e., motions of the bristles that are directed parallel to the tooth flanks, can be comparatively increased.

In some implementations, the spring constant of the spring device may be greater along an axis of motion, along which the poking motions of the brush head are carried out, than along an axis of motion, along which the wiping motions of the brush head are carried out parallel to the tooth flanks.

It is advantageous to adapt the spring device, particularly its spring constants in the mutually perpendicular directions, and the driving frequency of the drive, to one another in such a way that the drive carries out an essentially elliptical driving motion or, if applicable, an approximately oval driving motion or, in general terms, a driving motion in the form of a flattened circle.

The drive can advantageously features adjusting means for adjusting its driving frequency such that the driving frequency can be adapted to the respective spring device and manufacturing tolerances in the drive and/or the spring device, as well as deviations of the vibration frequency resulting thereof, can be compensated.

In an additional implementation, the suspension, particularly its spring device, and the drive itself are realized in such a way that the amplitude of the driving motion in a first direction is preferably at least five-times higher than the amplitude of the driving motion in a second direction extending perpendicular thereto. If the drive carries out the aforementioned elliptical vibratory or oscillatory motion, the longitudinal axis of the motion ellipse may be at least five-times longer, preferably more than ten-times longer, than the lateral axis of the motion ellipse.

The spring device does not necessarily have to be aligned in accordance with the oscillatory motion of the drive. In an additional implementation, the spring device has two principal axes with different spring constants, both of which lie in a plane that extends transverse to the longitudinal axis of the toothbrush and may simultaneously form the plane of motion of the drive.

According to one advantageous embodiment, the spring consists of a labyrinth spring with spring arms that are designed differently from each other in order to realize the different spring constants. It would be possible, in particular, to provide spring arms of different lengths that result in the dissimilarity of the spring constants.

The labyrinth spring may be realized, in particular, in an approximately disk-shaped or plate-shaped fashion. The spring device may be advantageously accommodated in the housing of the toothbrush essentially perpendicular to the longitudinal axis of the toothbrush.

In order to simplify the assembly and to ensure the desired alignment of the spring device and therefore the correct orientation of the different spring constants in different directions, the spring device may feature an orientation coding that makes it possible to install the spring device in the housing in a predetermined alignment. The orientation coding and/or the corresponding housing section may be realized in such a way that the spring device can only be installed in one predetermined alignment. This makes it possible to ensure, for example, that the lower amplitude of the driving motion occurs in the poking direction and the higher amplitude of the driving motion occurs in the wiping direction. If so required, the orientation coding on the spring device and/or the corresponding housing section, on which the spring device can be mounted, may also allow several predetermined installation positions in order to reverse the directions, in which the higher amplitude and the lower amplitude occur, e.g., for different applications. However, the preferred embodiment is the above-described embodiment, in which the spring device can only be installed in one predetermined alignment.

The spring device may feature, in particular, a mounting carrier that preferably consists of a frame with the corresponding orientation coding. The frame may suitably deviate from the rotational symmetry in order to ensure that the spring is installed in the desired direction.

The aforementioned mounting carrier or, in particular, mounting frame may be advantageously realized integrally with the aforementioned labyrinth spring. According to one particularly advantageous embodiment, the spring device may consist of a sheet metal stamping, wherein several of these sheet metal stampings that are preferably realized congruently may, if applicable, be stacked on top of one another in order to form a spring assembly of sorts.

In an additional embodiment, the drive is not only suspended by means of the aforementioned spring device, but also connected to the housing at another coupling point. In a further embodiment, the transmission element and/or the drive connected thereto may, in particular, be coupled to the housing in a multiaxially pivoting fashion by means of a bearing, preferably an elastic sleeve. In this case, the bearing advantageously forms a rigid coupling on the housing similar to a ball-and-socket joint such that the transmission element and/or the drive connected thereto can carry out a tumbling motion similar to a three-dimensional rocker on a conical orbit. It goes without saying that the conical orbit does not have to have a circular cross section, but advantageously can be in the form of an elliptical cone in the above-described fashion.

The transmission element is coupled similar to a ball-and-socket joint in the above-described fashion, in particular, at a center or intermediate section, such that the transmission element describes a double-conical orbit when it is set in motion by the drive. In this case, the transmission element may extend through the housing in an opening on the face of the hand part housing and extend out of the hand part on its face, wherein the bearing is advantageously arranged in the region of the through-opening. A brush head, particularly an exchangeable brush, can be advantageously attached or coupled to the protruding section of the transmission element. It is advantageous that the section of the transmission element situated in the interior of the housing is rigidly connected to the drive or a drive chassis accommodating the drive, on which the aforementioned spring device engages.

In an additional embodiment, the spring device is arranged on the side of the drive chassis that lies opposite to the bearing. It would also be conceivable, in principle, to arrange the spring device between said bearing and the drive. However, the spring device is preferably arranged on the side of the drive that faces away from the transmission element. Due to this measure, the spring device has a longer lever arm referred to the bearing that respectively defines the conical or double-conical motion path of the transmission element. Consequently, an effective control of the driving motion can be realized with low spring forces and a compact and lightweight spring device can be used.

In one advantageous embodiment, the drive consists of an electric motor with an imbalance, e.g., in the form of an eccentrically arranged mass. The imbalance is driven in a rotational fashion such that an oscillating vibratory motion is achieved.

In order to realize a precise transmission of the spring forces to the drive, the spring device can be positively and/or non-positively connected to the drive or to a drive chassis accommodating the drive, preferably in a non-wobbling fashion. In this case, the spring device may, in particular, be riveted to the drive or its drive chassis, respectively.

Due to the movable support of the entire drive and the corresponding relative motion between the housing and the drive, the transmission means of the energy supply and/or the control needs to allow the corresponding motions. In this respect, it would be possible, in principle, to use elastic lines or, if applicable, even sliding contacts. In some implementations, the power supply of the drive and/or its control device features rigid connecting points on the housing for connecting the movably supported drive in the immediate vicinity of the bearing, by means of which the transmission element and the drive are respectively coupled to the housing. Almost no relative motions occur in the immediate vicinity of this coupling point because this location quasi forms the root of the double-conical motion path of the drive and the transmission element connected thereto. The rigid connecting points of the power supply and the control device on the housing consequently lie in a region in which the motion amplitude of the drive train is very low.

In this respect, it is particularly advantageous to realize the transmission means in the form of metal strips that connect the electric terminals of the motor to the rigid connecting points on the housing. The metal strips allow the aforementioned motions that essentially consist of an angular offset at the aforementioned location. The drive may be connected, in particular, to a printed circuit board that extends as far as the vicinity of the bearing of the transmission element by means of the aforementioned metal strips.

BRIEF DESCRIPTION OF THE DRAWINGS

FIG. 2 shows a longitudinal section through the hand part of the electric toothbrush according to FIG. 1 along the line B-B in FIG. 1;

FIG. 3 shows a longitudinal section through the hand part according to the preceding figures along the line A-A in FIG. 2;

FIG. 4 shows a schematic front view of the brush head of the toothbrush according to FIG. 1 that elucidates the motion path of the brush head;

FIG. 5 shows a cross section through the hand part of the toothbrush along the line F-F in FIG. 2, wherein this cross section shows the suspension of the drive on the housing by means of a labyrinth spring, and FIG. 6 shows an enlarged top view of the spring device of the suspension for the drive of the toothbrush according to the preceding figures.

DETAILED DESCRIPTION

Figure 1:
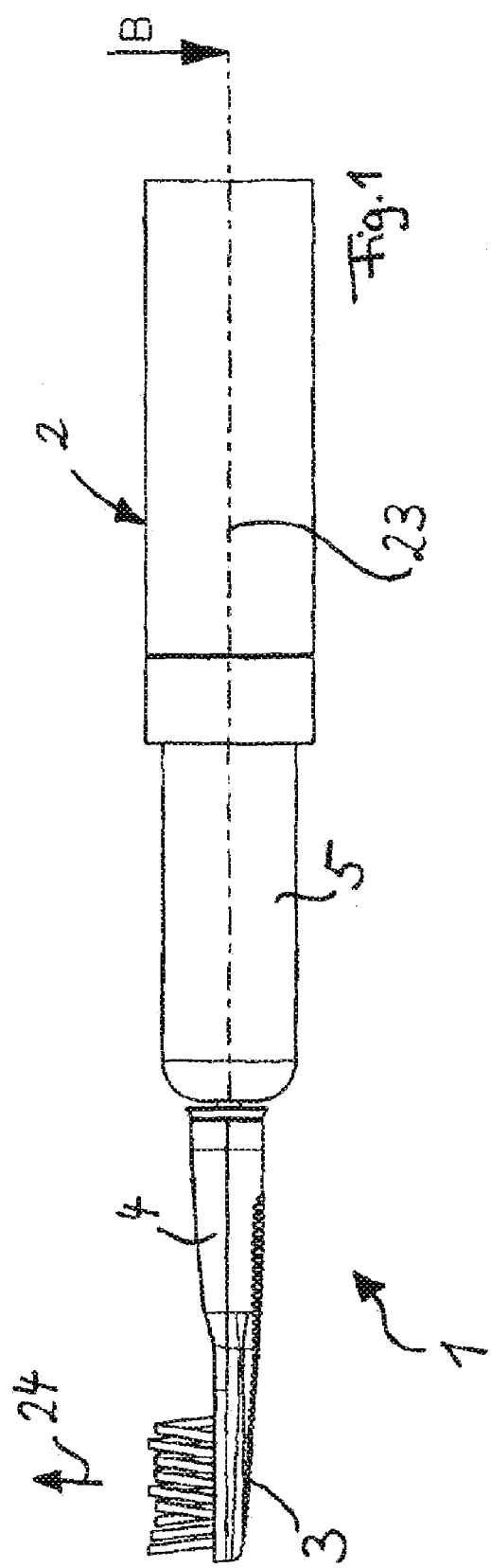
FIG. 1 shows a schematic side view of an advantageous embodiment of an inventive electric toothbrush with a hand part and a clip-on brush that can be attached thereto.

The electric toothbrush 1 illustrated in the figures comprises a hand part 2, to which a brush head 3 can be attached, wherein the brush head 3 in the embodiment shown comprises a brush tube 4, by means of which the brush head 3 can be attached to the hand part 2.

The hand part 2 comprises an essentially tubular housing 5 that accommodates an electric drive 6, as well as an energy source therefor, particularly in the form of a battery or an accumulator, and may also feature not-shown actuating and control elements.

According to FIGS. 2 and 3, the drive 6 is arranged in the front section of the interior of the housing 5 of the hand part 2 and comprises a transmission element 7 in the form of a rigid rod that protrudes from the face of the housing 5 through a through-opening 8. The aforementioned brush head 3 can be attached to the protruding section of the transmission element 7 with its brush tube 4, wherein the transmission element 7 and the brush head 3 feature suitable coupling means 9, for example, in the form of clip-on means in order to connect the brush head 3 to the transmission element 7 in a torsionally and flexurally rigid fashion.

In the region of the through-opening 8, the transmission element 7 is arranged in an elastic sleeve 10 seated in the aforementioned through-opening 8. This sleeve 10 forms a pivot bearing similar to a ball-and-socket joint and enables the transmission element 7 to carry out three-dimensional vibratory motions relative to the housing 5, but largely fixes the transmission element 7 axially. The sleeve 10 allows, in particular, a double-conical motion path of the transmission element 7, the contacting cone points of which lie in the region of the sleeve 10.

The aforementioned transmission element 7 is rigidly connected to a drive chassis 11, particularly in a flexurally rigid fashion, such that the transmission element 7 carries out the same motions as the drive chassis 11. The drive chassis carries the actual drive 12 that consists of an electric motor 13 with an imbalance 14 in the form of a mass that is eccentrically arranged on the motor shaft in the embodiment shown. The end of the drive chassis 11 that faces away from the transmission element 7 is elastically suspended on the housing 5 by means of a spring device 15. The spring device 15 preferably consists of the labyrinth spring 16 that is illustrated in detail in FIG. 6.

In the embodiment shown, the spring 16 features a central mounting section 17 that is coupled to an outer mounting section 20 by means of spring arms 18 and 19 such that the central mounting section 17 can be moved relative to the outer mounting section 20 by deforming the spring arms 18 and 19. It is advantageous to rigidly mount the central mounting section 17 on the drive 12, particularly the face of the drive chassis 11, namely in a positive and non-positive fashion. In this case, it would be possible, in principle, to use a screw connection. However, it is preferred to rivet the spring 16 to the drive chassis 11.

On the other side, the spring 16 is firmly clamped in the housing 5 with its outer mounting section 20. According to FIG. 6, the mounting section 20 consists of a peripheral, essentially rectangular mounting frame, on the opposite limbs 20a and 20b of which the aforementioned spring arms 18 and 19 are fixed. According to FIGS. 2 and 3, the aforementioned mounting frame 20 may be clamped between two sections of the housing 5. For example, the mounting frame 20 may be clamped between the abutting housing halves that are screwed to one another.

In this case, the mounting frame 20 advantageously comprises an orientation coding 21 that cooperates with an orientation coding on the housing 5 in such a way that the spring device 15 needs to be installed in a predetermined alignment relative to the housing. Suitable asymmetries may serve as orientation coding 21 in this case. In the embodiment shown, the orientation coding 21 consists of a tab-shaped projection on the mounting frame 20 and a corresponding recess in the housing. The aforementioned tab-shaped or lug-shaped projection can engage into the corresponding recess in the housing 5 such that the alignment of the spring device 15, particularly the rotatory alignment relative to the longitudinal axis 23 of the toothbrush, is defined.

The spring constant or spring stiffness of the spring device 15 is realized differently along different axes. According to FIG. 6, the spring arms 18 and 19 are respectively realized in an essentially L-shaped fashion, wherein the two limbs of each spring arm 18 and 19 have different lengths. In this case, the two spring arm sections 18a and 19a that respectively extend essentially parallel to the X-axis are shorter than the spring arm sections 18b and 19b that essentially extend parallel to the Y-axis and therefore essentially perpendicular to the aforementioned spring arm sections 18a and 19a. Consequently, the spring 16 shown in FIG. 6 has a lower spring stiffness in the direction of the X-axis than in the direction of the Y-axis. Accordingly, the drive 6 coupled to the central mounting section 17 can be displaced easier and farther in the direction of the X-axis (see FIG. 6) than in the direction of the Y-axis. The difference between the spring constants along the X-axis and the Y-axis of the spring 16 can basically be chosen differently and is preferably adapted to the design and the driving frequency of the drive 6. The spring stiffness of the spring 16 in the direction of the Y-axis is advantageously at least 25% higher than the spring stiffness in the X-direction.

With respect to the installation alignment of the spring device 15 that is defined by the orientation coding, it is advantageous that the higher spring stiffness is realized in the direction that corresponds to the poking direction or the principal direction 24 of the bristles of the brush head 3 while the lower spring stiffness extends in the direction of the X-axis and essentially perpendicular to the longitudinal axis 23 of the toothbrush and the aforementioned principal direction 24 of the bristles of the brush head 3. In order to elucidate this arrangement, the alignment of the X- and Y-axes of the spring device 15 is illustrated in FIG. 4 that shows a front view of the brush head 3.

Due to the thusly achieved suspension of the drive 6 that has a different stiffness in different directions, the imbalance 14 (eccentric mass) causes the drive to describe an essentially elliptical motion path 25 (see FIG. 4), the longitudinal axis of which is preferably about ten-times to thirty-times longer than its lateral axis (see FIG. 4), preferably about twenty-times longer. In this case, the highest amplitude essentially occurs in the aforementioned X-direction while the lowest amplitude of the oscillatory motion occurs in the aforementioned Y-direction. Consequently, the bristle section on the brush head 3 only carries out a slight poking motion in accordance with the oscillation in the Y-direction, but a more significant wiping motion with a higher amplitude parallel to the tooth flanks in accordance with the oscillation in the X-direction. The elliptical motion path illustrated in FIG. 4 may also assume a different angular position relative to the x- or y-axis, but the poking motion in the y-direction should still be significantly smaller than the wiping motion in the x-direction.

According to FIGS. 2 and 3, the vibratory motion of the drive 6 along the elliptical motion path illustrated in FIG. 4 is converted into a tumbling motion of the transmission element 7 on a double cone, the contacting cone points of which lie in the region of the bearing sleeve 10. It goes without saying that the rotating oscillatory motion of the brush head 3 may be greater than the oscillatory motion of the drive 6 in accordance with the lever ratios.

The driving frequency of the drive 6 is advantageously adapted to the spring constants of the respective spring device 15 used in order to compensate manufacturing tolerances of the spring and the drive in such a way that the desired elliptical oscillatory motion is achieved. In order to adjust the speed or driving frequency of the drive 6, the drive may be controlled by means of an adjustable voltage stabilization circuit that makes it possible to stabilize and adjust the supply voltage of the electric motor 13 to the correct value.

The power supply and the control of the electric motor 13 are advantageously not realized with conventional wires, but rather with metal strips 27 that lead from the motor terminals to rigid connections 28 on the housing and advantageously lie in the region of the bearing sleeve 10 and therefore in the region, in which the motion amplitude of the transmission element 7 is very low, i.e., practically zero. It would be possible, in particular, to provide a printed circuit board with the rigid housing connections 28, to which the metal strips 27 are connected, on the face of the housing 5, namely in the region of the through-opening 8 provided at this location.

Other embodiments are within the scope of the following claims.

The invention claimed is:

1. A hand part of an electric toothbrush having a brush head, the hand part comprising:
   a housing,
   a drive that is elastically mounted on the housing by a spring device and that can be moved with an oscillatory driving motion in at least one plane of motion, and
   a transmission element that is connected to the drive,
   wherein the spring device has different spring constants in two different directions in the plane of motion of the drive such that the oscillatory motion of the brush head has different amplitudes in these directions, and wherein the spring device and the driving frequency of the drive are adapted to one another in such a way that the brush head carries out an elliptical driving motion.

2. The hand part according to claim 1, wherein the drive can be moved along an elliptical motion path, the longitudinal axis of which is at least five-times longer than the lateral axis.

3. The hand part according to claim 1, wherein the drive comprises an adjustment device configured to adjust its driving frequency.

4. The hand part of claim 3 wherein the adjustment device comprises an adjustable voltage stabilization circuit.

5. The hand part according to claim 1, wherein the driving motion of the drive has a lower amplitude in the direction of a poking motion than in a lateral direction extending perpendicular thereto.

6. The hand part according to claim 1, wherein the spring device has two principal axes with different spring constants, both of which lie in a plane that extends transverse to the longitudinal axis of the toothbrush.

7. The hand part according to claim 1, wherein the spring device has a greater spring constant along a first axis of motion than along a second axis of motion generally perpendicular to the first axis of motion.

8. The hand part according to claim 1, wherein the spring device comprises a labyrinth spring having spring arms of different lengths.

9. The hand part according to claim 1, wherein the spring device comprises a disk-shaped member that extends in a plane that lies substantially perpendicular to the longitudinal axis of the toothbrush.

10. The hand part according to claim 1, wherein the spring device comprises a mounting carrier clamped in the housing.

11. The hand part according to claim 1, wherein the spring device includes an orientation coding such that the spring device can be installed in the housing in a predetermined alignment.

12. The hand part according to claim 1, wherein the spring device includes integral mounting sections for mounting the spring device on the drive or the housing.

13. The hand part according to claim 1, wherein the spring device comprises a sheet metal stamping.

14. The hand part according to claim 1, wherein at least one of the transmission element and the drive is coupled to the housing in a multiaxially pivoting fashion by a bearing.

15. The hand part according to claim 14, wherein the spring device is arranged on the side of the drive that lies opposite to the bearing.

16. The hand part of claim 14 wherein the bearing comprises an elastic sleeve.

17. The hand part according to claim 1, wherein the transmission element is coupled to a through-opening section on the housing.

18. The hand part according to claim 1, wherein the transmission element is rigidly connected to the drive.

19. The hand part according to claim 1, wherein the drive features an electric motor with an imbalance.

20. The hand part of claim 19 wherein the imbalance is provided by an eccentrically mounted mass.

21. The hand part according to claim 1, wherein the spring device is positively connected to the drive.

22. The hand part according to claim 1, wherein the drive is movably suspended and is connected to rigid connections on the housing.

23. The hand part according to claim 22, wherein the drive includes terminals, and the terminals of the drive are connected to the rigid connections on the housing by flat metal strips.

24. The hand part of claim 1 wherein the at least one plane of motion is transverse to the longitudinal axis of the toothbrush.

25. An electric toothbrush having a removably mounted brush head, the electric toothbrush comprising:
   a hand part comprising a housing, a drive that is elastically mounted on the housing by a spring device and can be moved with an oscillatory driving motion in at least one plane of motion, and a transmission element that is connected to the drive and configured to transmit the driving motion to the brush head,
   wherein the spring device has different spring constants in two different directions in the plane of motion of the drive such that the oscillatory motion of the brush head has different amplitudes in the these directions, and wherein the spring device and the driving frequency of the drive are adapted to one another in such a way that the brush head carries out an elliptical driving motion.

26. The electric toothbrush according to claim 25, wherein the spring device has a greater spring constant along an axis of motion that extends substantially parallel to a principal longitudinal direction of bristles of the brush head relative to the spring constant transverse to this principal longitudinal direction.

* * * * *